(12) United States Patent
Chou et al.

(10) Patent No.: US 6,748,345 B2
(45) Date of Patent: Jun. 8, 2004

(54) METHOD OF ANALYZING CRYSTALLINE TEXTURE

(75) Inventors: Cheng Tsien Chou, Oxford (GB); Keith Graham Dicks, Buckinghamshire (GB); Pierre Rolland, Les Ulis (FR)

(73) Assignee: Oxford Instruments Analytical Limited, Oxford (GB)

( * ) Notice: Subject to any disclaimer, the term of this patent is extended or adjusted under 35 U.S.C. 154(b) by 0 days.

(21) Appl. No.: 10/200,251

(22) Filed: Jul. 23, 2002

(65) Prior Publication Data

US 2003/0130803 A1 Jul. 10, 2003

(30) Foreign Application Priority Data

Jul. 23, 2001 (GB) .............................................. 0117892

(51) Int. Cl.[7] .............................................. G06F 19/00
(52) U.S. Cl. ........................ 702/207; 702/23; 378/70; 378/71; 378/73
(58) Field of Search ...................... 702/27, 23; 250/310, 250/307, 311; 378/71, 44, 45, 70, 73, 79, 81

(56) References Cited

U.S. PATENT DOCUMENTS 6,301,330 B1 * 10/2001 Kurtz et al. .................. 378/71
6,462,339 B1 * 10/2002 Michaluk et al. ........... 250/310
2003/0012334 A1 * 1/2003 Kurtz et al. .................. 378/73

* cited by examiner

Primary Examiner—John Barlow
Assistant Examiner—Hien Vo
(74) Attorney, Agent, or Firm—Staas & Halsey LLP (57) ABSTRACT

A method of analyzing crystalline texture from data defining the orientation of crystals in a sample of polycrystalline material including, for each crystal, determining the orientation of a first direction in the sample, with respect to a common reference frame fixed to the crystal structure of each crystal. A number of crystals sharing a similar orientation of the first direction with respect to the reference frame is selected and for each, the orientation is determined of a second direction in the sample with respect to the reference frame. A number of crystals sharing a similar orientation of the second direction with respect to the reference frame is selected and a crystal texture corresponding to the orientation of the selected crystals with respect to the first and second directions within the sample is determined and/or represented.

29 Claims, 4 Drawing Sheets

METHOD OF ANALYZING CRYSTALLINE TEXTURE

FIELD OF THE INVENTION

The present invention relates to a method of analysing crystalline texture.

BACKGROUND TO THE INVENTION

A wide range of materials have a crystalline structure and these include minerals, ceramics, semi-conductors, superconductors, metals and alloys. The vast majority of these materials are polycrystalline, that is composed from a number of component crystals which are often referred to individually as "grains".

The crystallographic orientations of the crystals in a polycrystalline sample relative to a fixed reference are seldom random. Where there is some preferred orientation of the crystals then the material is said to exhibit a "texture". Crystalline planes and directions are conventionally represented using Miller indices with {hkl} representing the crystal planes in terms of the normal to the crystal planes, and <uvw> representing the crystal directions within these {hkl} planes. The texture of a sample can therefore be represented by relating these crystalline planes and directions to corresponding physical directions with respect to the sample.

Conventionally a crystalline texture in a plate or thin film sample is represented as {hkl}<uvw>. These planes and directions are parallel to two corresponding orthogonal directions in the sample. In general this is arranged such that {hkl} represents the crystal plane normals which are parallel to the plane normal of the sample, known as the "normal direction" (ND), and <uvw> represents the crystalline directions within these planes that are parallel to a "longitudinal" or "rolling direction" (RD) within the sample. The samples are therefore prepared such that RD lies within the plane of the sample and ND is perpendicular to RD, and normal to the sample surface.

Crystalline texture is important in materials science as a number of material properties are dependent upon the orientations of the crystals. For example, silicon steels have directions of high magnetic permeability along their <100> crystal directions, a fact which is used in the production of transformer cores.

Traditionally the representation of textures in polycrystalline materials has been carried out using pole figure (PF) or Euler angle methods.

A pole figure can be regarded as a scatter plot showing how the respective crystals are oriented relative to an external frame of reference such as that of the sample. A specific direction with respect to the crystal structure is selected, and for each crystal in the sample this direction is plotted as a point on a stereographic projection (showing the intersection of the direction with a surrounding sphere).

The pole figure therefore represents a statistical distribution of a particular crystal direction, for all grains in which the crystallographic orientation is measured and plotted. The pole figure can be obtained by grain-by-grain measurements or collectively by polycrystalline diffraction using x-rays.

There are a number of problems associated with the use of pole figures. One of these is that the appearance of the pole figure is dependent upon the particular crystal direction plotted, due to the crystal symmetry. Considerable expertise and experience in crystallography is required to interpret pole figures, particularly as even a specific texture will have a different appearance depending upon the crystal direction that is plotted in the pole figure.

A further problem is that many of the points within the pole figure are actually related by the crystal symmetry and this makes the interpretation of the pole figures difficult because consideration of the crystal symmetry is also required.

When more than one texture is present within a sample, these textures are superimposed in the pole figures which makes their individual identification problematical. Whereas some common textures in simple crystal systems may be recognisable by an expert, pole figures showing more complicated textures such as those with large index values for {hkl} and/or <uvw>, or for less common crystal systems are much more difficult to interpret.

An alternative to pole figures is to use the Euler method in which consideration is made of the rotations to each crystal that would be required in order to bring each crystal into alignment with a particular orientation in the sample. The crystal orientations relative to the sample can be represented by three consecutive rotations (Euler angles) around selected orthogonal axes attached to the crystal.

These angles are represented as three rotations around orthogonal axes and each individual measurement of the crystal orientation in the sample is plotted as a point located in the resultant three dimensional "Euler angle" space. Using this method, the existence of texture will be marked by clusters of points in the space. As the space is three dimensional, this is usually displayed by a series of slices cut along one of the axes.

In a similar manner to the pole figure method, crystal symmetry makes interpretation of the Euler plot extremely difficult to visualise and understand, particularly with multiple or complicated textures and uncommon crystal systems.

There is therefore a need to simplify crystalline texture analysis such that crystalline texture information can be more readily obtained and interpreted without the high levels of skill and experience often required in known methods.

SUMMARY OF THE INVENTION

In accordance with a first aspect of the present invention we provide a method of analysing crystalline texture from data defining the orientation of crystals in a sample of polycrystalline material, the method comprising:

for each crystal, determining the orientation of a first direction in the sample, with respect to a common reference frame fixed to the crystal structure of each crystal;

selecting a number of crystals sharing a similar orientation of the first direction with respect to the reference frame;

for each selected crystal, determining the orientation of a second direction in the sample with respect to the reference frame;

selecting a number of crystals sharing a similar orientation of the second direction with respect to the reference frame; and determining and/or representing a crystal texture corresponding to the orientation of the selected crystals with respect to the first and second directions within the sample.

One advantage of the present invention is that it provides a method in which crystal texture can be determined and/or represented in such a manner that it is more easily interpreted. This is enabled by the use of a reference frame attached to the crystal structure rather than to the sample, and the determination of the orientations of first and second directions in the sample with respect to the crystals. Those crystals sharing a common orientation with respect to the sample are therefore selected and the texture may be represented and/or determined accordingly.

The method also enables the automation of the steps of determining the orientation of the crystals with respect to the crystal structure and indeed their selection. This can be performed by a suitably programmed computer.

Preferably the first and second directions are orthogonal, thereby allowing these directions to be related to the directions used by convention in describing crystalline texture.

Although the analysis of the crystal texture could be performed by computation, preferably the orientation of the first and/or second direction with respect to the reference frame, is displayed to a user of the system as an inverse pole figure (IPF). Typically separate IPFs are used for the first direction and second direction.

The use of the common reference frame is convenient for the purposes of presentation to the user in that, unlike the pole figure method, the information displayed is not dependent upon the pre-selection of a particular crystallographic direction. However, the first and second directions are chosen to define the orientation of the sample. Typically one of the first or second directions are arranged to be the rolling direction or longitudinal direction of the sample (RD) with the other corresponding direction being the normal direction of the sample (ND).

The use of inverse pole figures (IPF) is also particularly advantageous in that, due to crystallographic symmetry, rather than using a full stereographic projection, a unit triangle of the IPF projection can be selected as this represents all of the information within the IPF. Preferably therefore the inverse pole figures are displayed as unit triangles, the advantage being that crystallographically equivalent points are superimposed at the same position within the unit triangle of the IPF.

Unlike in prior methods, common directions within the crystals including equivalent directions related by symmetry, can therefore be represented as single points in the IPFs which greatly reduces confusion in their interpretation.

Using the data describing the orientation of each crystal in the sample, the orientation of a crystal is represented by the position of a data point in each of the IPFs for the first and second directions. Each data point in the IPF represents a measurement taken at a particular location on the sample although typically multiple measurements are made on a sample and plotted accordingly.

The data points in the IPFs may also be represented using colored regions reflecting the data point density as this density is indicative of crystal texture.

High density regions can be located automatically by analysis of the data, although preferably these are located visually in the IPFs by a user. Typically in either case, a region of high data density is selected and a point chosen within this region. An angular range about the point is defined and if necessary, the position of the point is adjusted until all points within the high density cluster are within this angular range. A crystal plane (including those related by symmetry) {hkl} equivalent to the point is then calculated. The angular range is chosen to account for experimental error in the data. Preferably an angle of less than 15 degrees is used. A similar angle is used in data selection in the IPFs for the normal direction and the rolling direction. Although data points of either the normal direction (ND) or the rolling direction (RD) can be selected first, preferably the IPF corresponding to the normal direction (ND) is used to select the first region.

Upon selection of such a region within a first IPF, in general only the data corresponding to the region within the defined angular range of the chosen point are then used in plotting the second IPF.

The selected data are typically used to plot corresponding data describing the orientation of the associated crystals with respect to the rolling direction (RD) in the form of the second IPF.

One or more crystal textures can be identified in the second IPF by locating high densities of data points. As crystal directions in a texture lie within a plane having an associated plane normal, preferably by defining the direction of the plane normal using the IPF for ND, the corresponding crystal directions can be searched for in the IPF for RD. This is subject to the constraint that the ND and RD directions are orthogonal (within experimental errors). If the selection is performed under the control of a user then typically the computer restricts the selection of the data to data points in accordance with this orthogonality limitation.

Following conversion of the selected RD IPF data into a crystal direction (and those related by symmetry) <uvw> Using the center of mass model, the data are preferably output as a texture in the form of crystallographic planes and directions, {hkl}<uvw>.

This process may be repeated a number of times for different regions of high data point density in the first and the second IPF in order to determine multiple textures present within the sample. These identified textures can be output as data or represented graphically for example by coloring crystals in an image according to their determined texture.

The method is not limited to crystals of a particular material phase and therefore multiple phase or multiple component materials can also be analysed and the texture determined for each.

The data defining the orientation of the crystals is generally obtained from diffraction and therefore the method preferably further comprises initially obtaining diffraction patterns from a number of the crystals in the sample. Typically electron diffraction patterns are obtained from each crystal, for example using a transmission electron microscope or scanning electron microscope. However electron back-scattered diffraction is preferably used as this provides a convenient method of obtaining a diffraction pattern from each of the crystals within the sample.

Automated analysis of these electron diffraction patterns, in conjunction with data describing the crystal structure, allows the orientation of the crystals to be determined and stored for later analysis. The crystal structure data is typically in the form of data describing lattice parameters, lattice types, point and space groups and atomic occupancies, and is stored in a database. Data can be generated for this purpose for each of the various crystal systems found in nature.

In order to improve visualization of crystal orientations in relation to sample topography and morphology, the method preferably further comprises obtaining an image of the sample, for example using a scanning electron microscope. Sometimes this image can be analyzed using image analysis methods to identify the separate crystals within a sample. When grain boundaries are not visible on such an image, crystal orientation data can be obtained on a fine grid of sample positions and changes in orientation used to determine grain boundaries. Alternatively, the individual orientations measured at each grid point can be color coded so that individual grains become visible as connected areas of similar color.

In one example, the image is processed so that only crystals with orientation corresponding to a particular texture are displayed within the image.

In accordance with a second aspect of the present invention we provide apparatus for analysing crystalline texture from data defining the orientation of crystals in a sample of polycrystalline material, comprising:

a store for containing data defining the orientation of crystals, and a processor arranged to perform the method according to the first aspect of the invention.

Preferably the apparatus is in the form of a computer such as a PC. This may be the same computer used to control an SEM in order to determine the orientation data such that the apparatus provides unified crystal imaging and texture analysis facility. The apparatus will preferably therefore also include means for determining the data defining the orientation of the crystals, such as an electron microscope, and preferably a scanning electron microscope (SEM) arranged to obtain electron back scattered diffraction (EBSD) patterns.

The apparatus also preferably further comprises a display for presenting to a user with determined orientations of the crystals with respect to the reference frame. This allows the presentation of the texture information to a user as well as possibly an image of the sample. Typically the apparatus will further comprise a selection device such as a keyboard or mouse to enable a user to select a number of the crystals when their orientations are presented on the display.

BRIEF DESCRIPTION OF THE DRAWINGS

Some examples of methods of analysing crystalline texture in accordance with the present invention will now be described with reference to the accompanying drawings, in which.

DETAILED DESCRIPTION OF THE PREFERRED EMBODIMENTS

Figure 1:
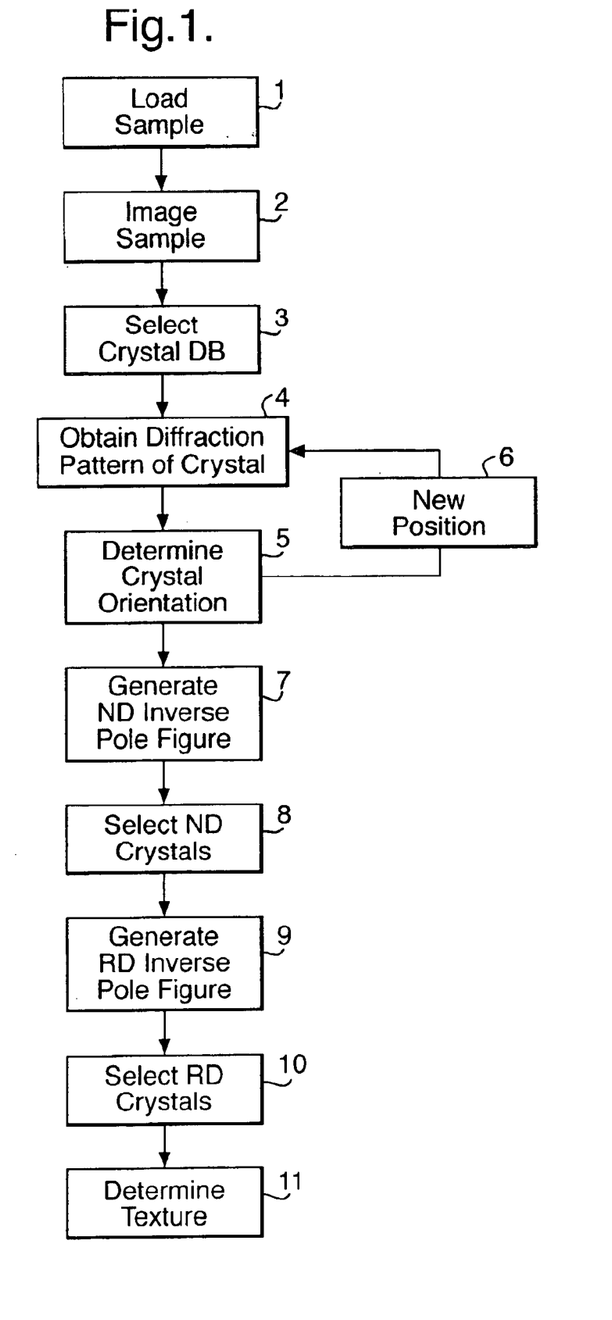
FIG. 1 is a flow diagram of the example method.

Referring to FIG. 1, a flow diagram is shown detailing a sample analysis procedure including the method according to the present invention.

A pre-prepared polycrystalline sample is loaded into the vacuum chamber of a scanning electron microscope (SEM) at step 1. The sample is of rolled polycrystalline titanium and is prepared and mounted such that the surface of the sample has a rolling direction (RD) within the plane of the sample surface. The sample surface is planar defining a normal direction (ND) that is normal to this surface.

The SEM is capable of imaging the sample in a number of imaging modes and is also equipped with the ability to produce an electron back-scattered diffraction pattern (EBSD). The SEM is controlled by a computer such as a PC or workstation.

The SEM vacuum chamber is then pumped down to an operational vacuum and the sample is oriented at a known angle to the SEM electron beam direction under computer control. It will be appreciated that the computer possesses detailed data describing the orientation of the sample, the electron beam and the detectors for use in imaging and in enabling an EBSD pattern to be produced.

An image of the sample surface is then obtained at step 2 for example using conventional secondary electron or back-scattered imaging. The image data are then retained by the computer for later use.

In the present example the sample is made from crystalline titanium and at step 3a crystal database is selected by the user of the computer, corresponding to the crystal structure of titanium. Typical data contained within the database include the lattice type, motif and unit cell dimensions for titanium which is used as described below, in the calculation of the positions and intensities of diffraction bands.

At steps 4 to 6, an electron back-scattered diffraction pattern is obtained at a number of points on the planar sample surface. In the present case these are arranged as a square array with the array pitch being much smaller than the typical crystal dimensions. However, when the statistics of crystal orientations is the main concern, the pitch can be chosen to be larger than the average grain size so a given number of measured points sample as many orientations as possible.

Steps 4 to 6 in FIG. 1 are performed at each point in the array as will now be described, before being repeated at the other points in the array.

When the electron beam in the SEM strikes the desired point upon the sample, an EBSD pattern is generated on a phosphor screen within the SEM at step 4. This is monitored using a low light level integrating CCD device. The CCD signal provides an image of the diffraction pattern for analysis by the computer.

The diffraction patterns formed on the screen take the form of Kikuchi bands which are pairs of near straight lines. The bands show the traces of the diffracted electron beam on the phosphor plate that satisfy the Bragg conditions. The relative spacing and angles of the bands contains information describing the orientation of the crystal under the electron beam, with respect to the beam and the phosphor screen.

At step 5, the orientation of the crystal is determined by software running on the SEM computer using the Kikuchi bands in the diffraction pattern and the crystallographic information contained in the titanium crystal database.

This is performed using an image processing routine known as a "Hough transform" in which each pair of bands in the pattern is transformed into a spot in "Hough space". The angular coordinates of the spot in Hough space provide the inclination angle of the Kikuchi band and the distance of the band to a selected origin.

In analysing the diffraction pattern, the software selects the three strongest Kikuchi bands in the pattern to form a triplet. The interplanar angles between each pair of the bands in the triplets are measured from the Hough transform of the pattern. They are then compared against a list of interplanar angles for the crystal calculated using the information in the crystal database. These angles can also be derived from spot positions in a spot diffraction pattern.

Having obtained these three angles (within a certain tolerance) then the software examines if a number of other strong Kikuchi bands in the pattern satisfy the calculated interplanar angles (also within the given tolerance). If these conditions are also satisfied, the crystal orientation is then given by nine direction cosines between the sample rolling direction (RD), transverse direction (TD), and normal direction (ND) and corresponding crystal directions. For cubic crystals, these crystal directions are [100], [010], and [001].

This orientation, which is in relation to the arrangement of the sample within the SEM, can then be converted into other orientations, and in particular the orientation of the crystal in question with respect to the surface of the sample.

Following the determination of the crystal orientation the calculated orientation data and the position of the measurement location within the sample are stored for example in RAM or in a file on a disc. The sample is then moved at step 6, relative to the electron beam, to the next position in the array of points to be sampled.

Steps 4 and 5 are then repeated at the new position although it should be noted that this new position may lie within the same crystal as the previous position and therefore a similar diffraction pattern would be expected to be obtained. Alternatively, the new position may be in an adjacent crystal and therefore the corresponding diffraction pattern obtained and the resultant orientation calculated will be different.

Once each point in the array has been sampled in terms of a diffraction pattern and crystal orientation, the data obtained and stored are then used in further steps 7 to 11 in order to determine whether any texture exists within the crystal.

The texture analysis in the present example is also performed using a computer system such as a PC. Although the analysis may be performed on a separate computer, in this case the SEM computer is used and is operated by a software application entitled "INCA CRYSTAL" written by Oxford Instruments Analytical Limited. The computer is equipped with conventional devices such as a keyboard, mouse, disc drive, memory and a color display such as a monitor.

At step 7, an inverse pole figure (IPF) is generated using the orientation data derived from the diffraction patterns and stored by the computer. As is known, an inverse pole figure (IPF) is a stereographic projection in which the coordinates of the stereographic projection are fixed with respect to the reference frame of the crystal structure. The crystal orientations are represented by plotting the position of a particular direction which is fixed in a reference frame not attached to the crystal. This direction is for example a direction within the sample. The IPF therefore relates the crystal reference frame to an external reference frame, which in this case is that of the sample.

In order to plot the IPF of step 7, the sample normal direction is chosen as this external direction. The orientation data for each point in the array are then used to calculate the direction of the sample normal direction within the common reference frame attached to each crystal. These are then plotted in the IPF for the normal direction (ND).

In the present example, the calculated ND IPF data are displayed on the display using colors to indicate the local density of the points representative of the position of the normal direction (ND) with respect to the crystals.

A sample with no texture whatsoever, (that is a random orientation of crystals), would therefore not show any clustering of the paints within a particular region of the IPF. However, this is rarely the case and regions on the display of higher spot density are colored red, lower spot density are colored green and lowest spot density are colored blue, using a continuous spectral color scale.

Rather than showing the full IPF as a circular sterographic projection, it is possible to represent this as a unit triangle. This is because the IPF is fixed to the frame of reference of the crystals rather than that of the sample. The crystal symmetry allows the entire stereographic projection of the IPF to be represented in a unit triangle, where points that would normally fall outside this triangle are plotted at their equivalent point within the triangle related by the known crystal symmetry.

Figure 2:
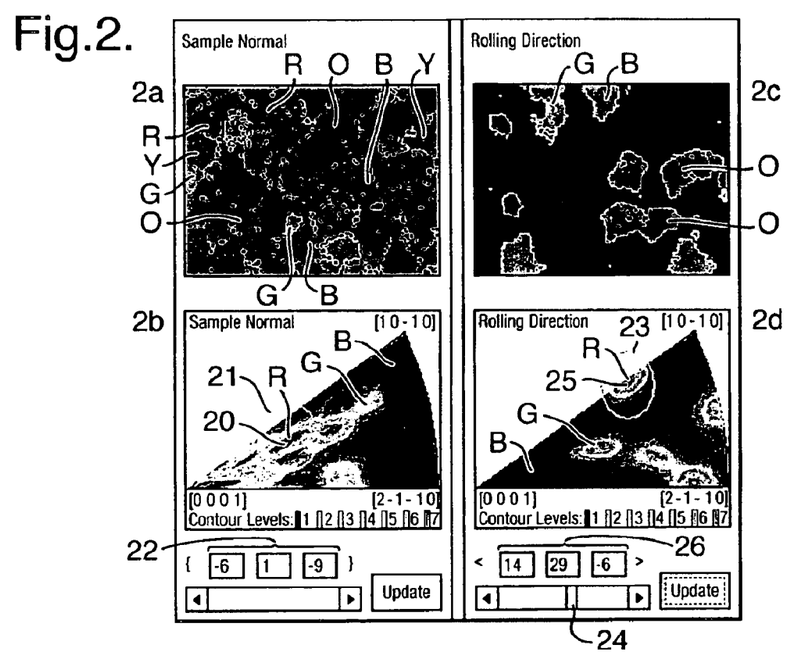
FIG. 2 is an example of a screen display showing an identified texture.

An example of the display showing the unit triangle IPF for the normal direction is shown in FIG. 2. It can be seen that display is split into quadrants denoted 2a, 2b, 2c, 2d and these are described below.

The ND IPF is shown in quadrant 2b. The unit triangle IPF is shown containing the orientation data calculated from the data sampled at each of the points in the array. The unit triangle corners are indexed in FIG. 2 using Miller indices in the four index format. The expansive darker shaded regions shown within quadrant 2b denote regions of low data point density. These are colored blue on the display and are labelled "B" in FIG. 2. Regions of intermediate data point density are shown in a lighter shade in FIG. 2 and these are colored green on the display (denoted by "G" in FIG. 2). The very highest density regions are indicated at regions of slightly darker shading surrounded by lighter shading in FIG. 2 and are colored red on the display (denoted by "R"). An example of such a high density region is indicated at 20.

A number of high density data point regions are shown in quadrant 2b. These show that the orientations of the crystals with respect to the normal direction (ND) of the sample, are not fully random.

At step 8 of FIG. 1, the user selects one of these regions for further analysis. This is performed using a circle 21 superimposed on the IPF which the user can position using the computer mouse. In doing so, each of the data points falling within the circle 21 are selected by the computer as a data set. In FIG. 2, the circle 21 in quadrant 2b is positioned to encircle the high density region 20. In this example the circle diameter denotes the 15 degrees tolerance angle. However, the user is free to choose any tolerance angle as appropriate.

The normal direction (ND) represented by each of the data points is used to calculate a representative normal direction for the data set selected, using a center of mass model.

The representative ND as calculated for the data set is then used to calculate the specific plane (including crystallographic equivalents) within the crystal that has a plane normal parallel to this direction. This plane {hkl} is presented to the user in the boxes 22 in terms of Miller indices.

Returning to FIG. 1, at step 9 a second IPF is then generated as shown in quadrant 2d of FIG. 2, using only the data set selected in step 8 (that is encircled by the circle 21). his second IPF is plotted with respect to the rolling direction (RD). Therefore for each data point selected with the circle 21, the orientation data are used to plot the position of the rolling direction for the corresponding array points with respect to the crystal reference frame. This produces the RD IPF shown in quadrant 2d, again represented as a unit triangle. The regions are colored according to their data point density on the display in a similar manner to the ND IPF in quadrant 2b. Examples of high (red), intermediate (green) and low (blue) data point density are labelled R, G, B in quadrant 2d of FIG. 2.

For a texture to be present within the crystalline sample, a common orientation of the crystals must be found with respect to at least two directions as at least two directions are required to fix the crystal orientation with respect to a frame of reference. Therefore if the second IPF shows clusters of data points within particular regions of the unit triangle, then there is a possibility that a texture may be present. However, a texture not only requires crystals to have an alignment of plane normals as there is a possibility that the crystals could be randomly orientated in angular rotation about a common plane normal. The second requirement for a texture is therefore that the crystal directions in crystals sharing a common plane normal are also aligned.

The crystal plane normals and crystal directions are necessarily orthogonal and therefore having obtained the plane normal parallel to the ND of the selected data set in step 8, a crystalline texture having this plane normal can be found by searching for clusters of those RD points within the RD IPF that are orthogonal to the plane normal direction. In the case when grains with RD parallel to <uvw> are chosen first, using an IPF showing the distribution of RD in the sample, then the {hkl} of the chosen grains that have the normals parallel to ND are said to belong to the zone with a common zone axis <uvw>. The {hkl} normals are in a plane perpendicular to <uvw>.

Referring to FIG. 2, it can be seen that the RD IPF unit triangle shown in quadrant 2d contains a number of regions having clustered data points (high density), although the presence of these high density regions is not conclusive of the presence of a texture. A further orthogonality constraint is therefore applied.

The user is aided in the selection of such regions by the computer. Again a circle 23 is used to select the regions of high data point density. The computer only allows the user to move the center of the circle 23 along a path which represents an orthogonal direction to the crystal plane normal that was calculated to be parallel to the sample normal direction in step 8. The user is provided with a slide bar 24 shown in the quadrant 2d of FIG. 2 to move the circle 23 along this constrained path. The user can alternatively click at a point in the second IPF to choose a region of high data point density, the computer then automatically selects the closest point along the path to position the circle.

A region of high density data points 25 (red) falling upon this path is shown in quadrant 2d and, at step 10 in FIG. 1, these are selected by the user.

A direction for the RD within this cluster is then calculated subject to the constraint that it is orthogonal to the ND of the data step selected in step 8. A tolerance angle of usually less than 15 degrees is permitted within this calculation. This calculated RD direction is then converted into a crystal direction that lies within the plane parallel to the normal direction calculated in step 8, within the experimental tolerance permitted.

A candidate texture is therefore obtained and can be expressed in terms of {hkl}<uvw> at step 11. The texture determined in relation to FIG. 2 is indicated by the integers within the boxes 22 and 26 denoting {hkl} and <uvw> respectively.

An enhanced image of the crystals within the sample (obtained at step 2 in FIG. 1) is shown in quadrant 2a of FIG. 2. The image presented in quadrant 2a comprises the image obtained in step 2 following the application of image analysis to identify the boundaries of the crystals. These are colored in accordance with their determined orientation according to step 5. The colors are assigned according to the (r, theta) position within the unit triangle using linear interpolations based upon r and theta. Examples of the crystals having different colors are labelled R, O, Y, G, B denoting red, orange, yellow, green and blue respectively.

The crystals in the image having a normal direction lying within the circle 21 selected in step 8 are presented in the quadrant 2c. Some examples of these crystals are labelled in quadrant 2c of FIG. 2 according to their color in a similar manner to quadrant 2a.

The system may be used to repeatedly select regions of the IPF for the normal direction and corresponding regions within the IPF for the rolling direction.

Figure 3:
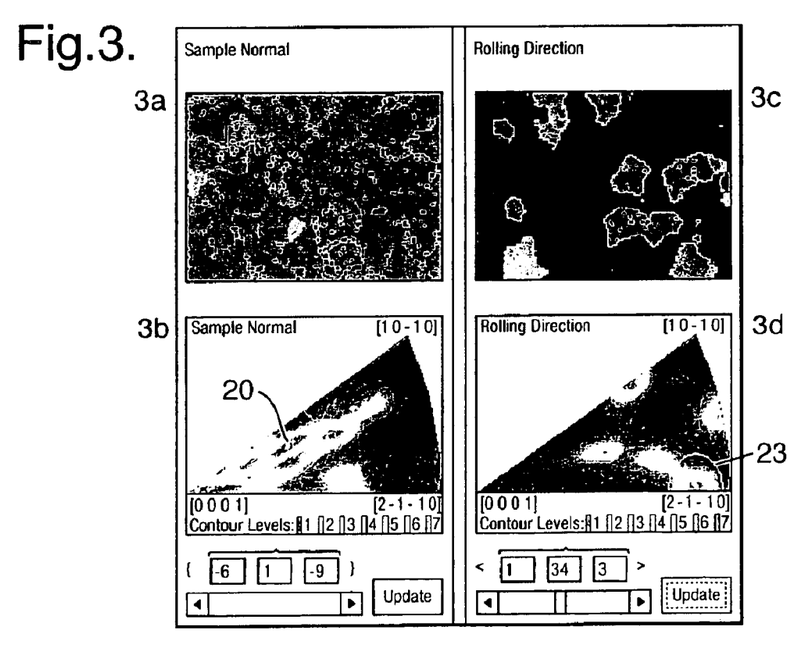
FIG. 3 shows a second identified texture with the same normal direction.

FIG. 3 is an example in which the selected ND region is identical to that of FIG. 2 (as shown in quadrant 3b). However, a second set of data points are shown encircled by the circle 23 in a different position of the RD IPF in the quadrant 3d. These also fall within the orthogonality requirement with respect to the normal direction 21.

Referring to the {hkl} and <uvw> integer values presented in the boxes 22 and 26 in FIGS. 2 and 3, it can be seen that the normal direction for each is the same. It should be noted that the integer values of the crystal directions are not exactly perpendicular to the normal direction. However this is within the 15 degree tolerance angle built into the system.

In the quadrants 3a and 3c the images presented are identical to those shown in quadrants 2a and 2c of FIG. 2. The image in the quadrant 3c is the same as in 2c because the normal direction is identical.

Figure 4:
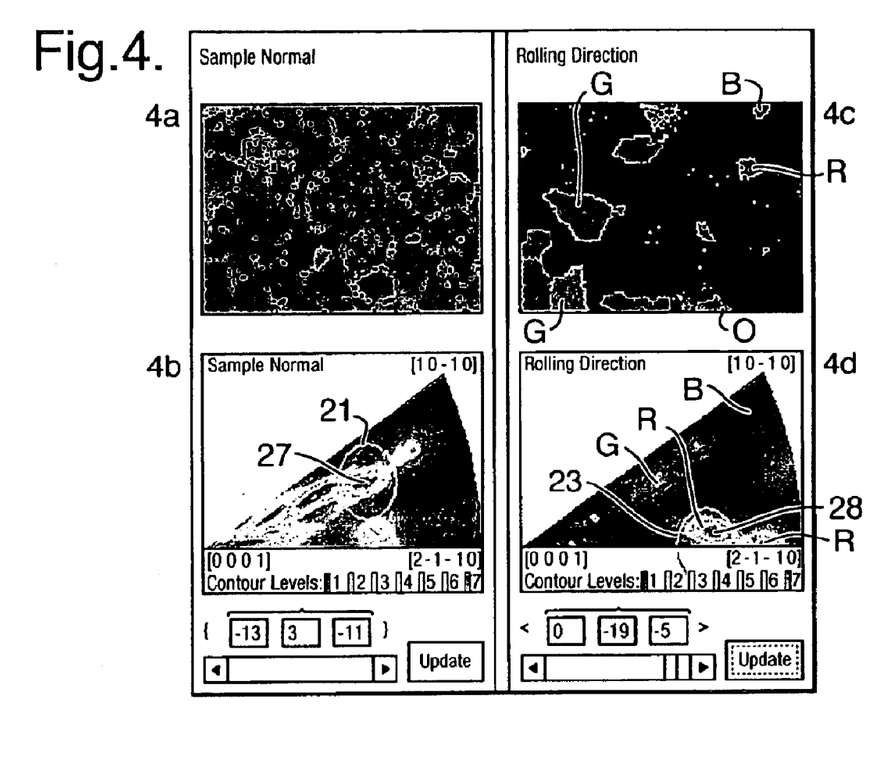
FIG. 4 shows a further texture having a different normal direction.

Referring to FIG. 4, in quadrant 4b a second high density data point region 27 is shown in the ND IPF and this is determined to be parallel to a different crystal plane normal, the plane normal indices being given in the boxes 22, 26. The corresponding IPF for the rolling direction is therefore different from those presented in FIGS. 2 and 3 with a corresponding different distribution of data points.

Again another candidate texture is found according to the orthogonality constraint as shown by the high density region 28 (red) encircled within the circle 23. The corresponding crystal direction is shown in the box 26. The quadrant 4a shows the image of the crystals in a similar manner to FIGS. 2 and 3 although in FIG. 4c a different set of crystals are highlighted and presented according to the different selected normal direction. Examples of the colors of the crystals on the display are labelled in a similar manner to FIGS. 2 and 3.

Figure 5:
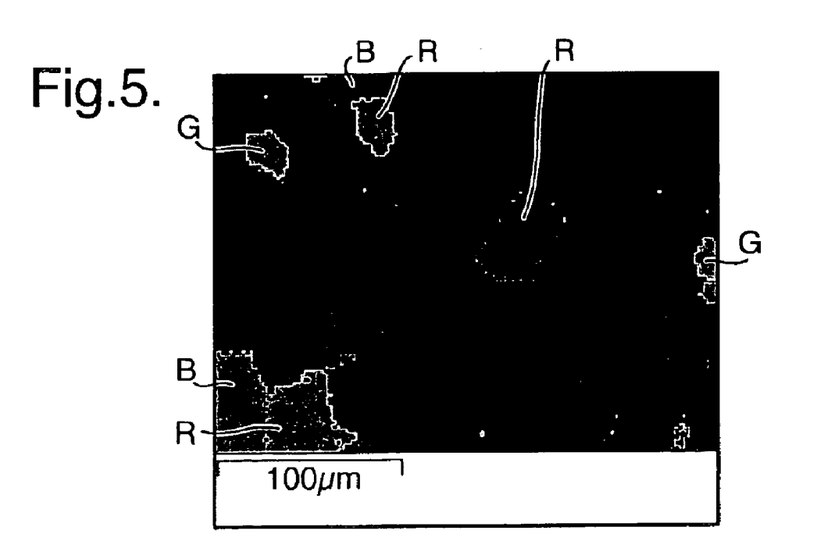
FIG. 5 shows an image of the crystals having the three identified textures.

As shown in FIG. 5, the system is capable of displaying crystals belonging to determined orientation relationships exclusively. In FIG. 5, crystals having the three determined crystal textures shown in FIGS. 2, 3 and 4 are shown in three different shades of greyscale. On the display these are presented using three corresponding colors, namely red (from FIG. 2), green (from FIG. 3) and blue (from FIG. 4), labelled R, G, B respectively. The determined numerical textures with respect to the normal direction and rolling direction of the sample are shown in Table 1 below, using both three and four index format.

Figure 6:
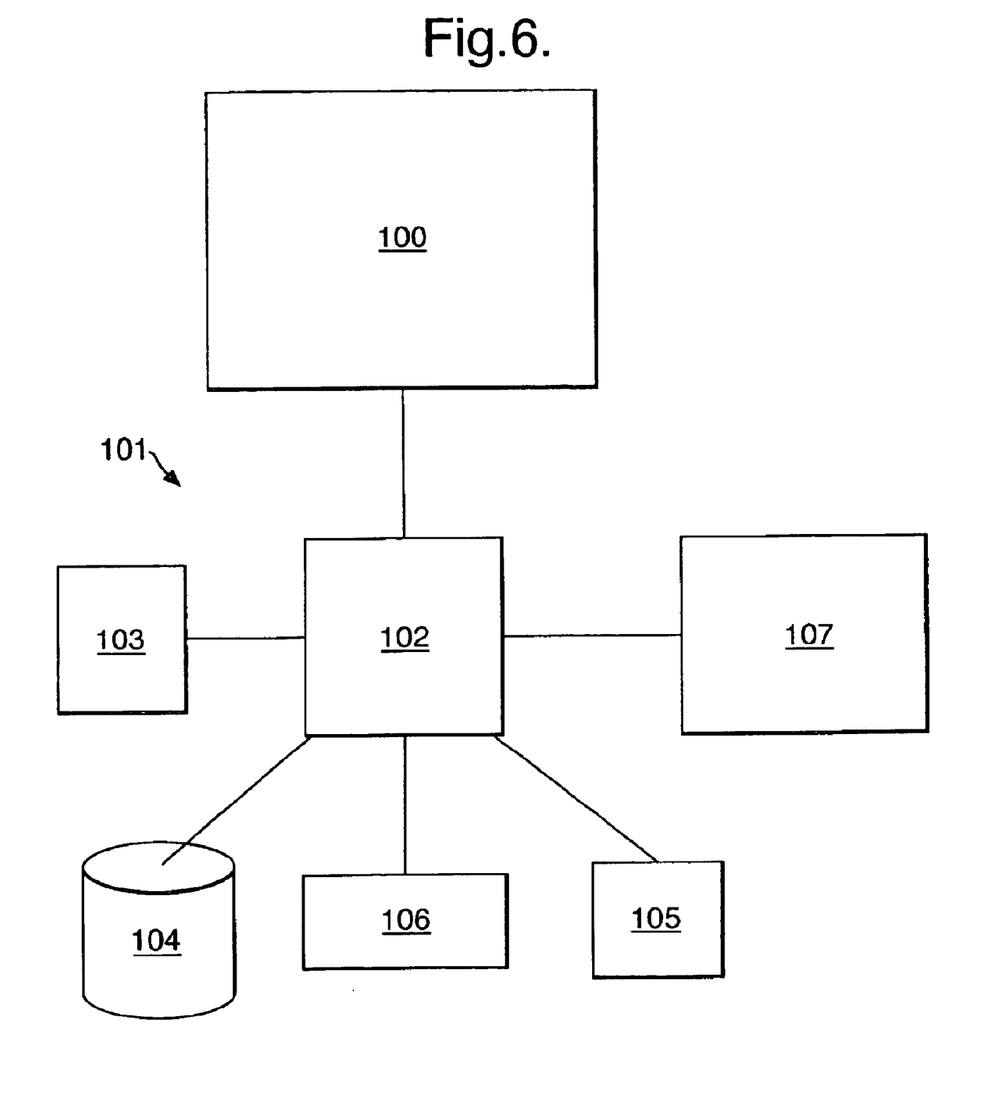
FIG. 6 is a schematic block diagram of the apparatus used for performing the example.

FIG. 6 is a block diagram of the apparatus according to the present example. The SEM is generally represented at 100, and includes apparatus such as a vacuum chamber containing the electron source, sample stage, detectors for imaging, along with the EBSD pattern detection apparatus including a phosphor screen and CCD.

This is connected to the control computer 101 which contains a processor 102. The computer has RAM 103, and is provided with access to the crystal database indicated at 104. In this case the database is stored on the computer 101, although it could be stored at a remote location. The processor 102 controls the SEM and calculates the crystal orientations using the data contained in the crystal database 104, in this case relating to the crystallography of titanium. The resultant data describing the orientations of the crystals are stored in a file on a disc drive 105. The input devices 106 which are operated by the user to control the system are also shown in FIG. 6. The display 107 in the form of a color monitor is used to present the color IPFs to the user, along with the processed color images of the sample, as shown in FIGS. 2 to 5.

Figure 7:
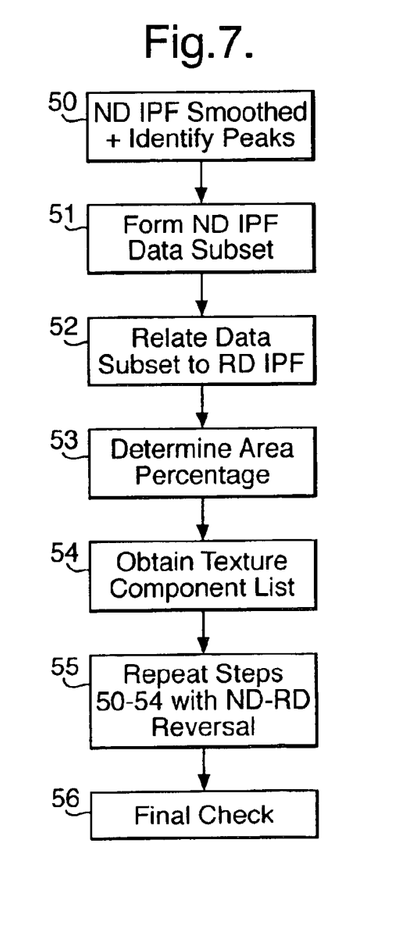
FIG. 7 is a flow diagram of an automated example method.

According to the present invention crystal orientation distributions (textures) in polycrystalline samples can now be determined automatically for the first time. This automatic determination is based on the newly developed method described above of consecutive inverse pole figures. Thus in an automated example of the method, the steps described below with reference to FIG. 7 are performed by a computer system such as the control computer 101.

At step 50 the data distribution in an IPF (e.g. ND) of the whole set of data is firstly smoothed by a filter of a given tolerance angle, the highly populated areas (peaks) on this smoothed IPF are located in turn, and the locations of the peaks are given approximate Miller indices {hkl}.

At step 51, for each of the peaks in this smoothed IPF a subset of data is formed by including the data that have angles with the location of the peak in the original IPF to less than the tolerance angle.

The data distribution in the second IPF (RD in this case) for a subset of data determined in the step 51, is then smoothed at step 52, using the method described in association with step 50. Peaks in this smoothed IPF are located in turn, and approximate Miller indices <uvw> are assigned to these peak locations. In the second IPF without smoothing, all data around each of the peaks that have angles with the location of peaks to less than the tolerance angle, form a subset of data representing texture components with different <uvw> but with a common {hkl}.

Following this, at step 53, the area percentage of a texture component {hkl}<uvw> is determined by the ratio between the number of data in the subset of data and the total number in the dataset.

When the above process is completed, at step 54 a list of texture components in the sample and their area percentages is obtained.

As indicated at step 55, the earlier steps 50 to 54 are carried out again, but the order of ND and RD in the first and the second IPFs is reversed.

At step 56 a final check is made to ensure that each of the texture components is not counted twice, and, two texture components are separated to an angle that is no smaller than the tolerance angle.

The present invention therefore provides a convenient and clear method of texture analysis that is capable of application to any crystal system. The method can also be automated allowing fast and accurate computation of crystal textures. Multiple textures within individual samples can be determined quickly without the need for great expertise in crystallography. The system is also equally applicable to simple and complicated textures (having high hkl and uvw indices).

TABLE 1

| Textures | {hkl}<br><uvw> | {HKIL}<br><UVW> |
|---|---|---|
| FIG. 2 (Red) | {−6 1 −9}<br><14 29 −6> | {−6 1 5 −9}<br><−1 44 −43 −18> |
| FIG. 3 (Green) | {−6 1 −9}<br><1 34 3> | {−6 1 5 −9)<br><−32 67 −35 9> |
| FIG. 4 (Blue) | {−13 3 −11}<br><0 −19 −5> | {−13 3 10 −11}<br><19 −38 19 −15> |

What is claimed is:

1. A method of analyzing crystalline texture from data defining the orientation of crystals in a sample of polycrystalline material, the method comprising:
    for each crystal, determining the orientation of a first direction in the sample, with respect to a common reference frame fixed to the crystal structure of each crystal;
    selecting a number of crystals sharing a similar orientation of the first direction with respect to the reference frame;
    for each selected crystal, determining the orientation of a second direction in the sample with respect to the reference frame;
    selecting a number of crystals sharing a similar orientation of the second direction with respect to the reference frame; and
    determining and/or representing a crystal texture corresponding to the orientation of the selected crystals with respect to the first and second directions within the sample.

2. A method according to claim 1, wherein the first and second directions are orthogonal.

3. A method according to claim 1, wherein the orientation of the first direction or the second direction with respect to the reference frame is displayed as a first inverse pole figure.

4. A method according to claim 3, wherein the orientation of the other direction of the first and second directions with respect to the reference frame is displayed as a second inverse pole figure.

5. A method according to claim 4, wherein the first and/or second inverse pole figure is displayed as a unit triangle.

6. A method according to claim 1, wherein the first direction is a rolling or longitudinal direction of the sample.

7. A method according to claim 6, wherein the second direction is the sample normal direction.

8. A method according to claim 1, wherein the selected crystals comprise all crystals having an orientation within less than substantially 15 degrees of a selected direction within the reference frame.

9. A method according to claim 1, wherein the method further comprises determining a direction representative of the similar orientations of the selected crystals.

10. A method according to claim 9, wherein the determination of the direction representative of the selected crystals is performed according to center of mass model.

11. A method according to claim 1, wherein at least one of the steps of selecting a number of the crystals is performed by a user.

12. A method according claim 1, wherein the step of selecting a number of crystals sharing a similar orientation with respect to the first and/or the second direction is performed automatically.

13. A method according to claim 1, further comprising repeating the method to determine and/or represent multiple textures of crystals within the sample.

14. A method according to claim 13, wherein the crystals comprise two or more distinct phases.

15. A method according to claim 1, wherein the method further comprises initially obtaining diffraction patterns from a number of the crystals in the sample.

16. A method according to claim 15, wherein the diffraction patterns are obtained using the electron back-scattered diffraction technique.

17. A method according to claim 1, further comprising obtaining an image of the sample.

18. A method according to claim 17, further comprising analysing the image to identify crystals within the image.

19. A method according to claim 18, further comprising displaying the image of the crystals and coloring the displayed crystals in accordance with their texture.

20. A method according to claim 18, wherein only the selected crystals are displayed from the image.

21. A method according to claim 1, wherein, when the crystal texture is determined, the method further comprises outputting the crystal texture as data identifying crystal planes and crystal directions.

22. A computer program comprising computer program code means for performing the method according to claim 1, when the computer program is run on a computer.

23. A computer program product comprising computer program code means stored on a computer readable medium for performing the method according to claim 1, when the computer program product is run on a computer.

24. Apparatus for analyzing crystalline texture from data defining the orientation of crystals in a sample of polycrystalline material, comprising:
  a store for containing data defining the orientation of the crystals, and
  a processor arranged to perform the method according to claim 1.

25. Apparatus according to claim 24, further comprising a display for presenting to a user the determined orientations of the crystals with respect to the reference frame.

26. Apparatus according to claim 24, further comprising a selection device for selecting a number of the crystals.

27. Apparatus according to claim 24, further comprising means for determining the data defining the orientation of the crystals.

28. Apparatus according to claim 27, wherein the means for determining the data defining the orientation of the crystals is an electron microscope.

29. Apparatus according to claim 28, wherein the electron microscope is a scanning electron microscope arranged to obtain electron back scattered diffraction patterns for use in determining the data defining the orientation of the crystals.

* * * * *